(12) United States Patent
Momoki

(10) Patent No.: US 11,517,263 B2
(45) Date of Patent: Dec. 6, 2022

(54) SENSOR, MEASURING APPARATUS, AND METHOD OF MANUFACTURING SENSOR

(71) Applicant: TERUMO KABUSHIKI KAISHA, Tokyo (JP)

(72) Inventor: Hideyuki Momoki, Hadano (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 709 days.

(21) Appl. No.: 16/560,523

(22) Filed: Sep. 4, 2019

(65) Prior Publication Data

US 2019/0388032 A1 Dec. 26, 2019

Related U.S. Application Data

(63) Continuation of application No. PCT/JP2018/002118, filed on Jan. 24, 2018.

(30) Foreign Application Priority Data

Mar. 21, 2017 (JP) .............................. JP2017-054991

(51) Int. Cl.
*A61B 5/00* (2006.01)
*A61B 5/145* (2006.01)
(52) U.S. Cl.
CPC .......... *A61B 5/6849* (2013.01); *A61B 5/1451* (2013.01); *A61B 5/14503* (2013.01);
(Continued)
(58) Field of Classification Search
CPC ..... A61B 5/6848; A61B 5/6849; A61B 5/145; A61B 5/14507; A61B 5/14551; A61B 5/14552; A61B 5/14532; A61B 5/14535; A61B 5/14539; A61B 5/14542; A61B 5/14546; A61B 5/1451; A61B 5/14503; A61B 5/1459; A61B 5/1468; A61B 5/1473; A61B 2562/12; A61B 2560/0462
See application file for complete search history.

(56) References Cited

U.S. PATENT DOCUMENTS

| 6,584,335 | B1 | 6/2003 | Haar et al. |
| 8,092,384 | B2* | 1/2012 | Meyer ................ A61B 5/14503 600/309 |
| 9,072,475 | B2 | 7/2015 | Hendriks et al. |

FOREIGN PATENT DOCUMENTS

| JP | H03-269358 A | 11/1991 |
| JP | H04-361152 A | 12/1992 |

(Continued)

OTHER PUBLICATIONS

International Search Report and Written Opinion dated Mar. 6, 2018 in International Patent Application No. PCT/JP2018/002118.

(Continued)

*Primary Examiner* — Chu Chuan Liu
(74) *Attorney, Agent, or Firm* — Foley & Lardner LLP

(57) ABSTRACT

A sensor includes: a needle member defining a hollow portion, wherein the needle member comprises a peripheral wall, and a through hole extends through the peripheral wall; an elongated detection member positioned in the hollow portion and extending along a longitudinal direction of the needle member; and at least one protruding portion that protrudes radially inward from the peripheral wall and restricts movement of the detection member in a radial direction.

14 Claims, 11 Drawing Sheets

(52) U.S. Cl.
CPC ... *A61B 5/14532* (2013.01); *A61B 2560/0462* (2013.01); *A61B 2562/12* (2013.01)

(56) References Cited

FOREIGN PATENT DOCUMENTS

| | | |
|---|---|---|
| JP | H06-509949 A | 11/1994 |
| JP | 2001-513350 A | 9/2001 |
| JP | 2003-038465 A | 2/2003 |
| JP | 2005-087613 A | 4/2005 |
| JP | 2012-130567 A | 7/2012 |
| JP | 2013-544570 A | 12/2013 |
| JP | 2016-168259 A | 9/2016 |
| WO | WO-92/17243 A2 | 10/1992 |
| WO | WO-2006/090596 A1 | 8/2006 |

OTHER PUBLICATIONS

International Searching Authority, "International Search Report," issued in connection with International Patent Application No. PCT/JP2018/002118, dated Mar. 6, 2018.

International Searching Authority, "Written Opinion," issued in connection with International Patent Application No. PCT/JP2018/002118, dated Mar. 6, 2018.

* cited by examiner

FIG. 5(b)                                    FIG. 5(c)

SENSOR, MEASURING APPARATUS, AND METHOD OF MANUFACTURING SENSOR

CROSS-REFERENCE TO RELATED APPLICATIONS

This is a bypass continuation of PCT Application No. PCT/JP2018/002118, filed on Jan. 24, 2018, which claims priority to Japanese Application No. 2017-054991, filed on Mar. 21, 2017. The contents of these applications are hereby incorporated by reference in their entireties.

The present disclosure relates to a sensor, a measuring apparatus, and a method of manufacturing the sensor.

BACKGROUND

A sensor is inserted into or embedded in the body of a subject such as a patient, and a component such as glucose in interstitial fluid of the subject is detected by the sensor as a substance to be measured.

WO 2006/090596 A discloses a biosensor that includes a needle-like hollow container as a needle member provided with a plurality of through holes on a lateral side thereof, a carrier cylinder inserted into the hollow container, and an optical fiber as a detecting member, the optical fiber having an end portion inserted into the carrier cylinder, the biosensor being to be indwelled in a subject.

SUMMARY

When the detection member inserted into the needle member collides with a peripheral wall of the needle member or the like, this collision may cause a decrease in measurement accuracy, breakage or the like. Thus, it is beneficial to restrict the movement of the detection member in the needle member. The detection member is required to be in good contact with liquid introduced into the needle member in order to ensure the detection of the substance to be measured. With the sensor disclosed in WO 2006/090596 A, there is a problem that the contact of the liquid with the detection member is prevented because the through hole is covered by the carrier cylinder.

In view of the above problems, an object of certain embodiments of the present disclosure is to provide a sensor, a measuring apparatus, and a method of manufacturing the sensor capable of restricting the movement of a detection member without preventing liquid from contacting the detection member.

A sensor according to one aspect of the present invention includes a needle member defining a hollow portion and having a through hole, and an elongated detection member positioned in the hollow portion and extending along an longitudinal direction of the needle member, and a peripheral wall of the needle member is provided with a protruding portion protruding inward in a radial direction of the needle member, and the protruding portion restricts the movement of the detection member in the radial direction.

In the sensor according to one embodiment of the present invention, the needle member includes the through hole in the peripheral wall, and the protruding portion is adjacent to the through hole along the longitudinal direction.

In the sensor according to the one embodiment of the present invention, the protruding portion is a cutout piece having a free end that is an end other than one end along the longitudinal direction, and the cutout piece includes an inclined wall portion extending inward in the radial direction from a side of the one end toward a side of the other end.

In the sensor according to the one embodiment of the present invention, in a case where the inclined wall portion is a first inclined wall portion, the cutout piece further includes a second inclined wall portion closer to the other end than the first inclined wall portion, the second inclined wall portion extending outward in the radial direction of the needle member from the side of the one end toward the side of the other end.

In the sensor according to the one embodiment of the present invention, the cutout piece is positioned inward in the radial direction from an outer peripheral surface of the peripheral wall.

In the sensor according to the one embodiment of the present invention, the cutout piece includes a top portion between the first inclined wall portion and the second inclined wall portion, the top portion being curved in a projecting shape inward in the radial direction.

The sensor according to the one embodiment of the present invention includes a plurality of the protruding portions, the plurality of protruding portions being positioned along a predetermined plane orthogonal to the longitudinal direction, and a radius of the detection member on the predetermined plane is larger than a minimum distance between the protruding portions adjacent to each other in a circumferential direction of the needle member.

The sensor according to the one embodiment of the present invention includes a plurality of the protruding portions, and the protruding portions provided at different positions in the longitudinal direction are arranged at different positions in the circumferential direction of the needle member.

In the sensor according to the one embodiment of the present invention, the detection member includes a detection unit, and the protruding portion is positioned at a position different from a position of the detection unit in the longitudinal direction.

A measuring apparatus according to one aspect of the present invention includes the above sensor.

A method of manufacturing a sensor according to one aspect of the present invention is a method of manufacturing a sensor including a needle member defining a hollow portion and having a through hole formed therein, and an elongated detection member positioned in the hollow portion and extending along an longitudinal direction of the needle member, and the method includes a protruding portion forming step of forming a protruding portion protruding inward in a radial direction of the needle member on a peripheral wall of the needle member and an inserting step of inserting the detection member from the hollow portion from the proximal end side.

According to the sensor, the measuring apparatus, and the method of manufacturing the sensor of certain embodiments of the present disclosure, it is possible to restrict the movement of the detection member without preventing liquid from contacting the detection member.

BRIEF DESCRIPTION OF THE DRAWINGS

FIGS. 5(a) through 5(c) are views schematically illustrating a second part of the method of manufacturing the sensor illustrated in FIG. 1.

DETAILED DESCRIPTION

Figure 1:
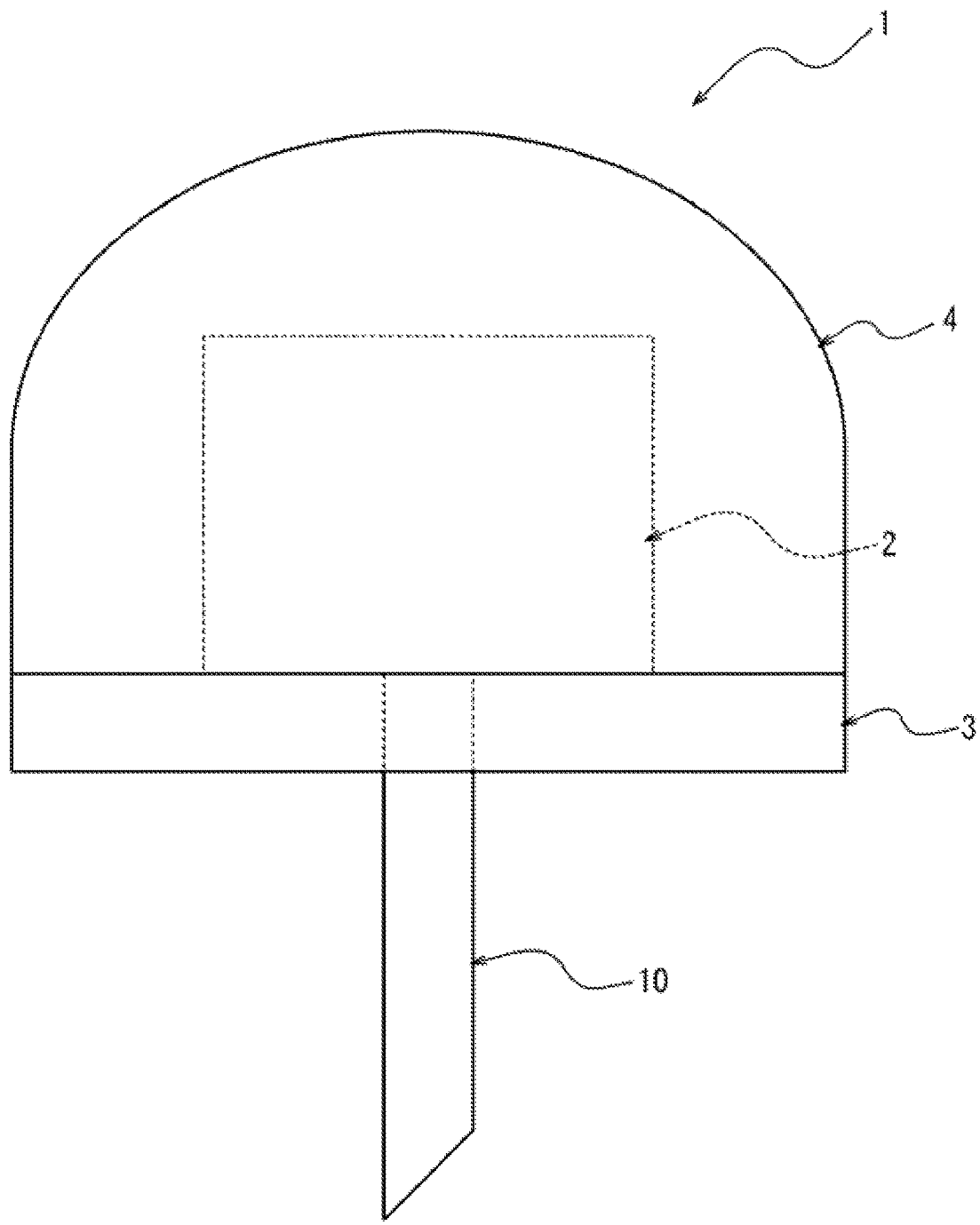
FIG. 1 is a schematic view illustrating a measuring apparatus according to a first embodiment.

Hereinafter, each embodiment will be described with reference to the drawings. The same reference numeral is given to common members in the drawings.

First Embodiment

Measuring Apparatus 1

FIG. 1 is a schematic view illustrating a measuring apparatus 1 according to a first embodiment. As illustrated in FIG. 1, the measuring apparatus 1 includes a sensor 10, a control unit 2, a support member 3, and a housing 4. The sensor 10 detects a substance to be measured and transmits information on a detection result to the control unit 2. The control unit 2 includes a processor, a memory, and the like, analyzes the detection result received from the sensor 10, and transmits an analysis result to an external display device or the like as needed. The support member 3 supports the sensor 10 on a proximal end side. The housing 4 houses the control unit 2 and engages with the support member 3. The measuring apparatus 1 is configured so that a distal end side of the sensor 10 can be discharged to the outside in a state in which the support member 3 and the housing 4 are engaged with each other.

Sensor 10

Figure 2:
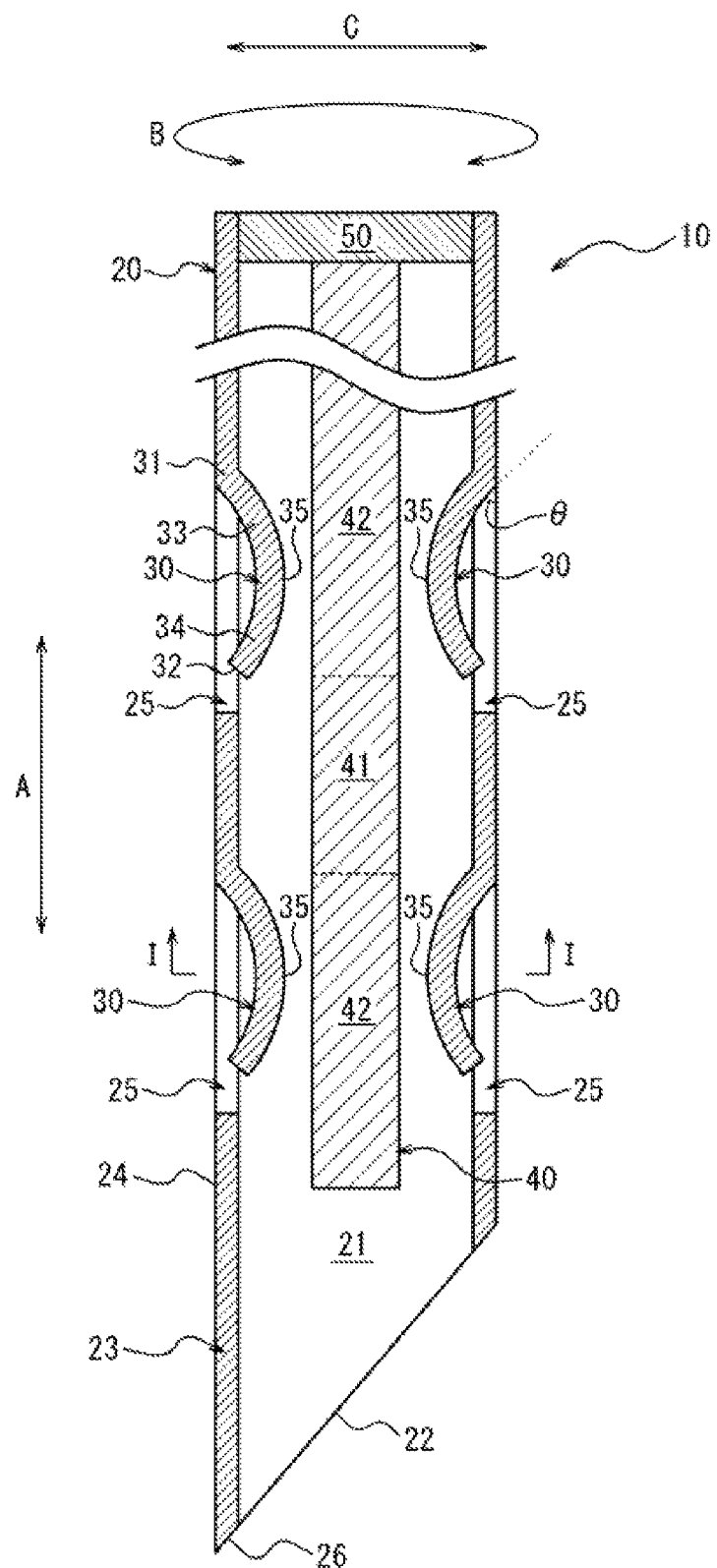
FIG. 2 is a longitudinal sectional view of the sensor illustrated in FIG. 1.
Figure 3:
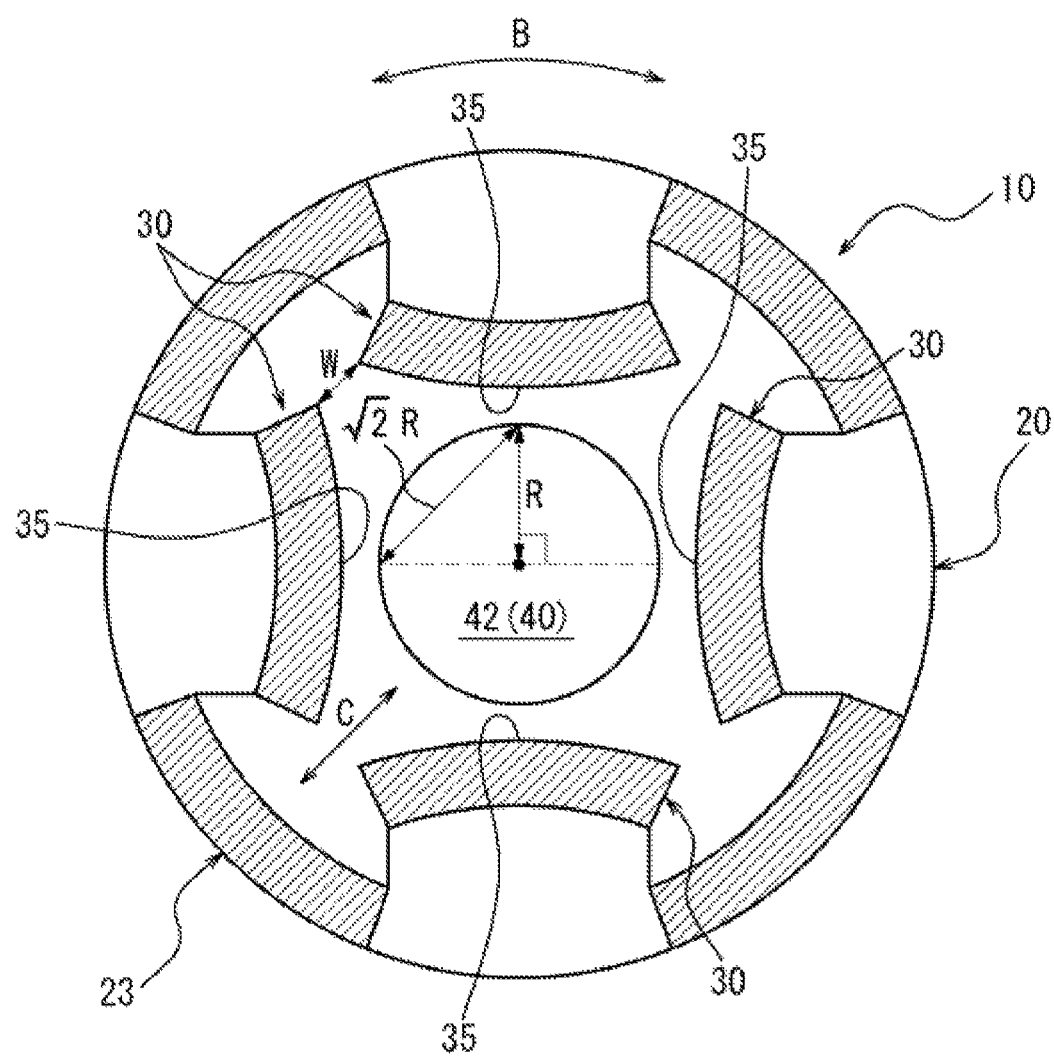
FIG. 3 is a cross-sectional view taken along line I-I of FIG. 2.

FIG. 2 is a longitudinal sectional view of the sensor 10. FIG. 3 is a cross-sectional view taken along line I-I of FIG. 2. As illustrated in FIG. 2, the sensor 10 includes a needle member 20, a detection member 40, and a fixing member 50.

The needle member 20 is a cylindrical hollow needle that defines a hollow portion 21 therein, has a thickness of 25 to 33 gauges (diameter of 0.5 mm to 0.2 mm) and a length of 1 mm to 10 mm, preferably a length of 3 to 6 mm. A blade surface 26 is formed at a distal end portion of the needle member 20. The blade surface 26 defines a distal end opening 22. On a peripheral wall 23 of the needle member 20, a plurality of through holes 25 for introducing body fluid such as interstitial fluid of a subject into the hollow portion 21 is formed. The hollow portion 21 communicates with the outside of the needle member 20 through the through hole 25 and the distal end opening 22. The peripheral wall 23 of the needle member 20 is provided with a protruding portion protruding inward in a radial direction C of the needle member 20. The protruding portion of the present embodiment is a cutout piece 30 formed on the peripheral wall 23. A size of the cutout piece 30 may be smaller than a size of the through hole 25.

Figure 7A:
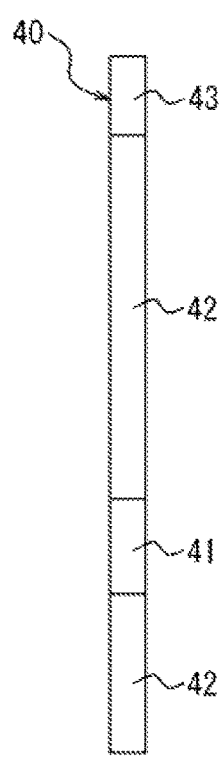
FIGS. 7(a) through 7(c) are views schematically illustrating a fourth part of the method of manufacturing the sensor illustrated in FIG. 1.
Figure 7B:
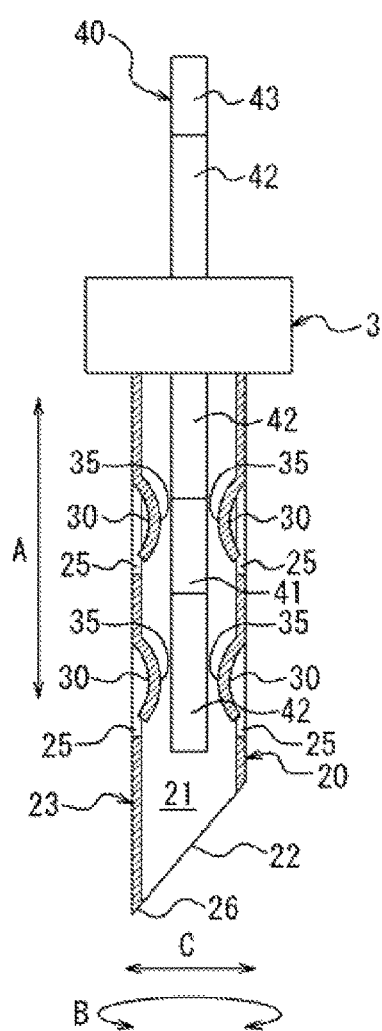
Figure 7C:
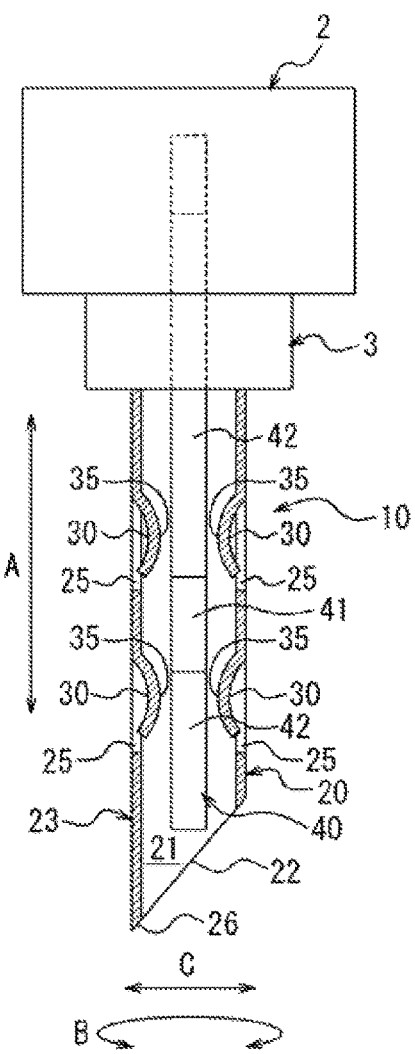

As the detection member 40, a member that detects an electrical signal according to an amount or concentration of the substance to be measured can be used. The detection member 40 is an elongated member. The detection member 40 is positioned in the hollow portion 21 and extends along an longitudinal direction A of the needle member 20. The detection member 40 is configured using a core member as a base and includes a detection unit 41 having an exterior of an outer wall of the core member, the exterior of the outer wall being configured to detect the substance to be measured and a protective portion 42 having an exterior of the outer wall of the core member, the exterior of the outer wall being coated with an insulating material. The detection unit 41 is a working electrode that detects a change in electrical characteristics of the substance to be measured. The detection unit 41 is formed on the surface of the core member by using a thin film forming means such as dipping, spray coating, electrolytic polymerization, and sputtering. The needle member 20 can be used as a reference electrode or a counter electrode with respect to the working electrode as the detection unit 41. The detection member 40 is provided, at a proximal end portion, with a connecting portion 43 penetrating the support member 3 and connected to the control unit 2 as described later with reference to FIGS. 7(a) through 7(c). Information on the substance to be measured detected by the detection unit 41 is transmitted to the control unit 2 via the connecting portion 43.

Alternatively, as the detection member 40, a member that detects an optical signal according to the amount or concentration of the substance to be measured can be used. The detection member 40 is an elongated member. The detection member 40 is positioned in the hollow portion 21 and extends from a proximal end side of the needle member 20 toward a distal end side of the needle member 20 along the longitudinal direction A (long axis direction) of the needle member 20. The detection member 40 is configured using, as a base, a core member excellent in light transmittance such as fluorocarbon resin, polymethylmethacrylate (PMMA), polycarbonate (PC), and cyclic olefins (COP). The detection member 40 includes the detection unit 41 having a part of the core member configured to detect the substance to be measured and the protective portion 42 having the exterior of the outer wall of the core member, the exterior of the outer wall being coated with a material having a lower refractive index than that of the core member. The detection unit 41 includes a fluorescent substance that detects a change in fluorescence characteristics due to a reaction with the substance to be measured included in the detection unit 41 and a substance that transmits the substance to be measured and protects a fluorescent substance, and the detection unit 41 is formed in a hole penetrating the core member. The detection member 40 is provided, at a proximal end portion, with a connecting portion 43 penetrating the support member 3 and connected to the control unit 2 as described later with reference to FIGS. 7(a) through 7(c). Information on the substance to be measured detected by the detection unit 41 is transmitted to the control unit 2 via the connecting portion 43. An excitation signal to the detection unit 41 can be transmitted from the control unit 2 via the connecting portion 43.

The fixing member 50 includes a fixing material such as an adhesive agent, and a position of the detection member 40 relative to the needle member 20 is fixed at a proximal end portion of the sensor 10. The detection member 40 is fixed by the fixing member 50 on the proximal end side but is not fixed on the distal end side. For this reason, at least a part of the distal end side of the detection member 40 can move outward (side of an outer peripheral surface 24) in the radial direction C in the needle member 20. The fixing member 50 is not limited to one that includes the fixing material such as an adhesive agent, but may be, for example, a fixing member 50 that is locked by the needle member 20 by, for example, being held and supported by the needle member 20.

Cutout Piece 30

Hereinafter, the cutout piece 30 will be described in detail. As described above, the cutout piece 30 as the protruding portion protrudes toward an inward direction of the needle member 20 (from the outer peripheral surface 24 to a central axis direction of the needle member 20 in the longitudinal direction A) in the radial direction C. Therefore, it is possible to restrict the movement of the detection member 40 outward in the radial direction C. Specifically, when the detection member 40 moves outward in the radial direction C, the detection member 40 abuts on the cutout piece 30 as the protruding portion, and the additional (further) movement of the detection member 40 outward in the radial direction C is restricted.

As illustrated in FIG. 2, the cutout piece 30 as the protruding portion is adjacent to the through hole 25 along the longitudinal direction A. Therefore, it is possible to suppress that the detection member 40 is damaged by contacting an edge or the like of the through hole 25 due to the cutout piece 30 as the protruding portion. Note that in the present embodiment, the cutout piece 30 is adjacent to the through hole 25 on the proximal end side of the needle member 20.

As illustrated in FIG. 2, the cutout piece 30 has a free end other than a proximal end 31 that is one end along the longitudinal direction A. In other words, while the cutout piece 30 is continuous with the peripheral wall 23 at the proximal end 31, the cutout piece 30 is discontinuous with the peripheral wall 23 at locations other than the proximal end 31 including a distal end 32 that is the other end. The through hole 25 is defined by a portion where the cutout piece 30 and the peripheral wall 23 are discontinuous with each other.

As illustrated in FIG. 2, the cutout piece 30 includes a first inclined wall portion 33 extending inward in the radial direction C from a side of the proximal end 31 toward a side of the distal end 32. Thus, the cutout piece 30 includes the first inclined wall portion 33 and a portion protruding inward in the radial direction C from the peripheral wall 23 is formed, whereby the outward movement of the detection member 40 in the radial direction C can be restricted by abutting on the cutout piece 30. Therefore, it is suppressed that the detection member 40 contacts the edge or the like of the through hole 25. To maintain a strength against force applied in the longitudinal direction A, a degree θ between the first inclined wall portion 33 and the peripheral wall 23 at the proximal end 31 is preferably less than 45 degrees in the longitudinal cross sectional view of the sensor 10.

As illustrated in FIG. 2, the cutout piece 30 includes a second inclined wall portion 34 extending outward in the radial direction C closer to the distal end 32 than the first inclined wall portion 33 from the side of the proximal end 31 toward the side of the distal end 32. Thus, the cutout piece 30 includes the second inclined wall portion 34, whereby it is possible to suppress that the detection member 40 contacts the distal end 32 and is damaged by burrs of the distal end 32 or the like.

As illustrated in FIG. 2, the cutout piece 30 includes the distal end 32 positioned inward in the radial direction C from the outer peripheral surface 24 of the peripheral wall 23 of the needle member 20. For this reason, the distal end 32 does not protrude outside the needle member 20, and a pain felt by the subject at the time of puncturing can be reduced.

As illustrated in FIG. 2, the cutout piece 30 includes a top portion 35 between the first inclined wall portion 33 and the second inclined wall portion 34, the top portion 35 being curved in a projecting shape inward in the radial direction C. For this reason, even in a case where the detection member 40 moves to contact the cutout piece 30, it is possible to suppress that the detection member 40 is damaged by the top portion 35 curved in a projecting shape. In the cross sectional view of FIG. 2, in the cutout piece 30 as the protruding portion of the present embodiment, not only the top portion 35 but also the first inclined wall portion 33 and the second inclined wall portion 34 are curved in a projecting shape inward in the radial direction C. More specifically, in the cross sectional view illustrated in FIG. 2, the cutout piece 30 of the present embodiment has a uniform arc-shaped cross section by the first inclined wall portion 33, the top portion 35, and the second inclined wall portion 34.

As illustrated in FIG. 2, the cutout piece 30 as the protruding portion is positioned at a position different from a position of the detection unit 41 of the detection member 40 in the longitudinal direction A. For this reason, even if the detection member 40 moves to contact the cutout piece 30, it is possible to suppress that the detection unit 41 directly contacts the cutout piece 30. Therefore, it is possible to suppress that measurement accuracy decreases due to a change in an area where the detection unit 41 contacts a non-measurement substance and that a glucose detection reagent applied to the detection unit 41 is damaged (peeled) by contacting the cutout piece 30. The top portion 35 of the cutout piece 30 may be configured to always abut on the protective portion 42, whereby the movement of the detection unit 41 is suppressed. As a result, by holding the detection member 40 at a predetermined position in the needle member 20, the sensitivity of the sensor 10 can be maintained. By coating the protective portion 42 with a wear resistant material such as a resin, the sensitivity of the sensor 10 can be maintained better. Examples of the resin include polyurethane, fluorine resin (polytetrafluoroethylene (PTFE), fluorinated ethylene propylene (FEP), perfluoroalkoxy alkane (PFA)), polyethylene terephthalate (PET), polyimide, silicone, cellulose, cellulose acetate, polyacrylonitrile (PAN), polymethylmethacrylate (PMMA), polypropylene (PP), and polyvinyl chloride (PVC).

Figure 4A:
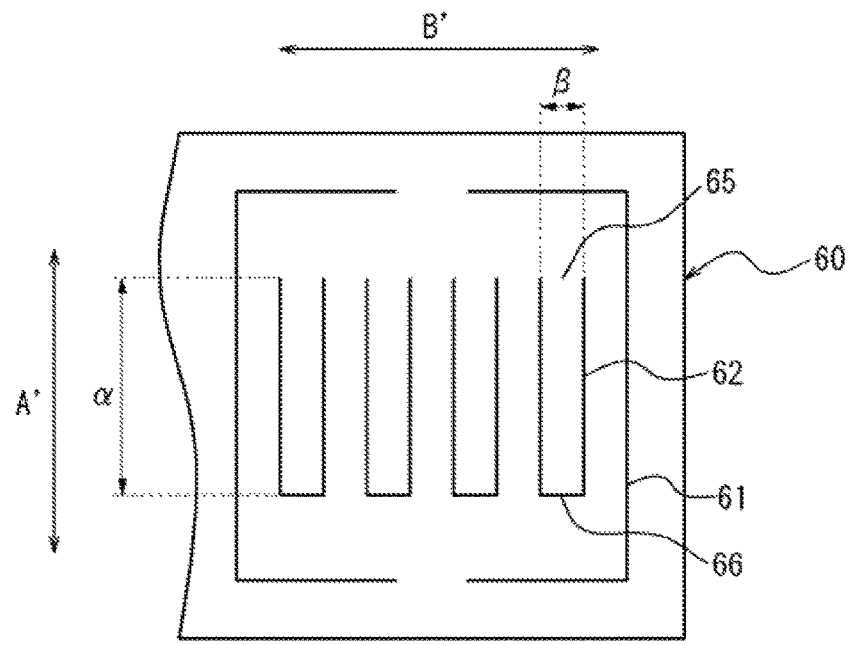
FIGS. 4(a) through 4(c) are views schematically illustrating a first part of a method of manufacturing the sensor illustrated in FIG. 1.

As illustrated in FIGS. 2 and 3, the sensor 10 includes a plurality of cutout pieces 30. As illustrated in FIG. 3, the sensor 10 includes a plurality of cutout pieces 30 along a circumferential surface of a plane orthogonal to the longitudinal direction A. It is preferable that a distance between the cutout pieces 30 along a circumferential direction B is substantially equal distance, and the detection unit 41 is reliably held in the needle member 20 at this place. As illustrated in FIG. 3, relationship between a radius R of the detection member 40 (protective portion 42) and a minimum distance W between the cutout pieces 30 adjacent to each other in the circumferential direction B of the needle member 20 in a plane along I-I line satisfies relationship of W≤R×√2. Therefore, even in a case where the detection member 40 moves outward in the radial direction C, since the detection member 40 simultaneously abuts on the top portion 35 of the cutout piece 30 adjacent in the circumferential direction B, the detection member 40 does not enter between the cutout pieces 30 adjacent to each other. Therefore, it is possible to reliably restrict that the detection member 40 moves until the detection member 40 abuts on the peripheral wall 23 without abutting on the plurality of cutout pieces 30. Even in a case where the cutout piece 30 is formed, for example, by punching the peripheral wall 23, a punched-out cross section of the cutout piece 30 does not easily contact the detection member 40. Therefore, it is possible to suppress that the detection member 40 contacts the punched-out cross section of the cutout piece 30 and is damaged. Although FIG. 2 illustrates an example in which the sensor 10 includes the cutout pieces 30 at two different positions in the longitudinal direction A, the sensor 10 may include the cutout pieces 30 at three or more different positions in the longitudinal direction A. As illustrated in FIGS. 4 to 6 described later, the sensor 10 may include the cutout piece 30 at only one location in the longitudinal direction A. The sensor 10 preferably includes the cutout pieces 30 and the through holes 25 at a plurality of positions also in the longitudinal direction A of the needle member 20. The sensor 10 preferably has a configuration in which the detection unit 41 is positioned between the plurality of cutout pieces 30 in the longitudinal direction A of the needle member. With such a configuration, the detection unit 41 of the detection member 40 can be brought into contact with body fluid efficiently.

Method of Manufacturing Sensor 10

Figure 4B:
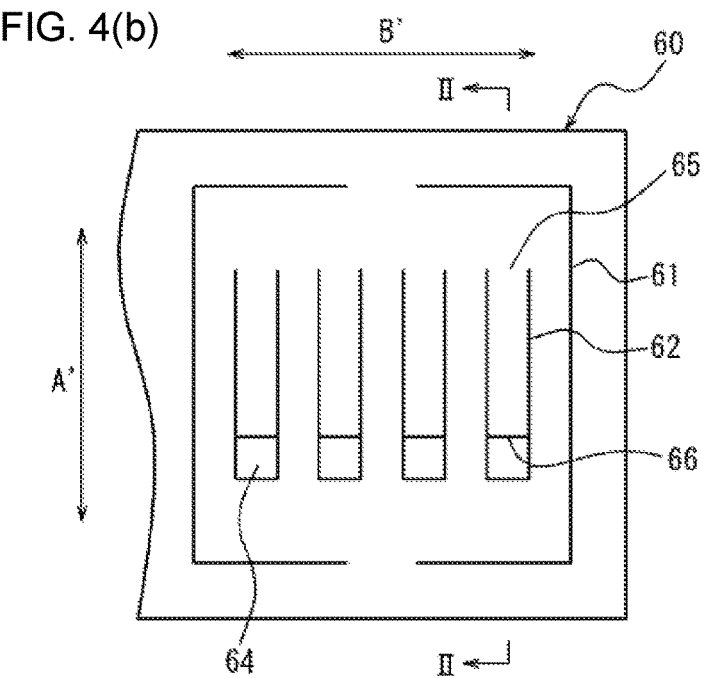
Figure 4C:
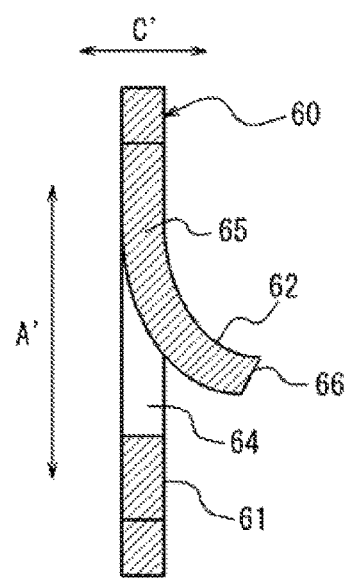
Figure 5A:
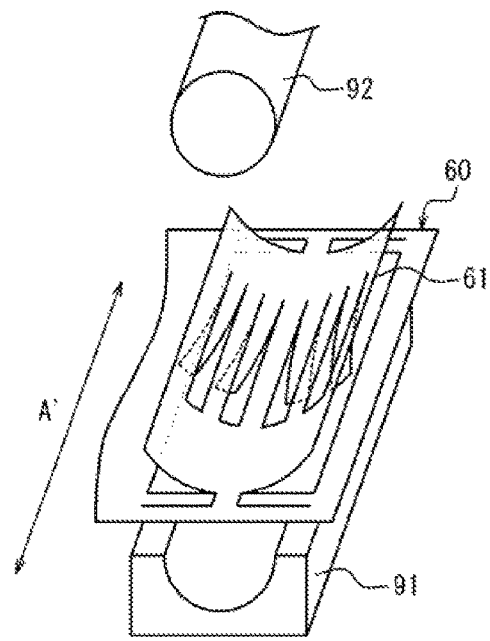
Figure 5A:
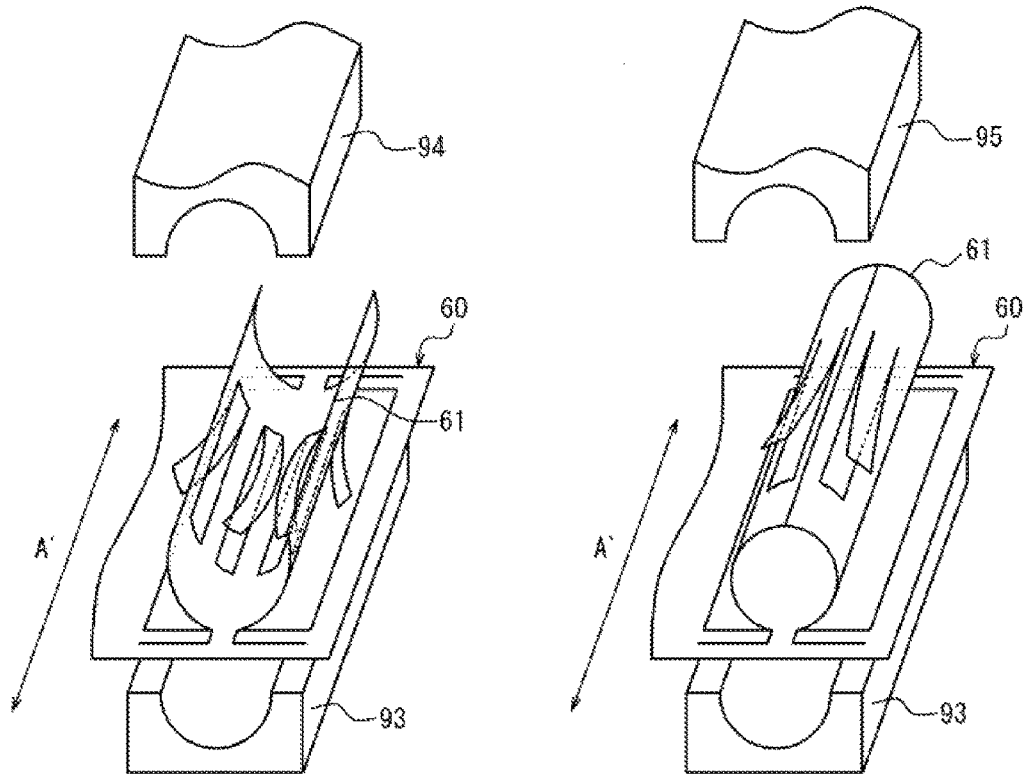
Figure 6A:
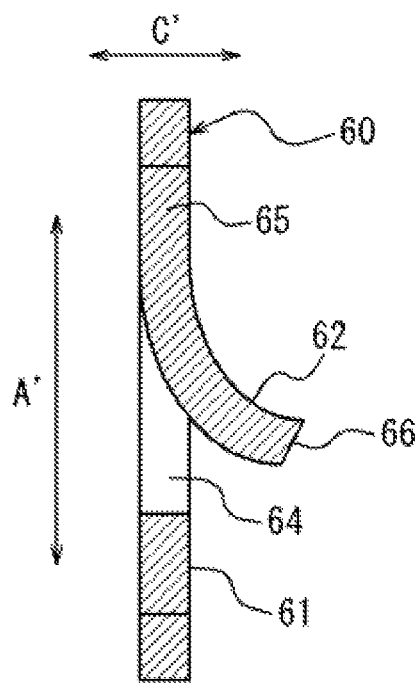
FIGS. 6(a) and 6(b) are diagrams schematically illustrating a third part of the method of manufacturing the sensor illustrated in FIG. 1.
Figure 6B:
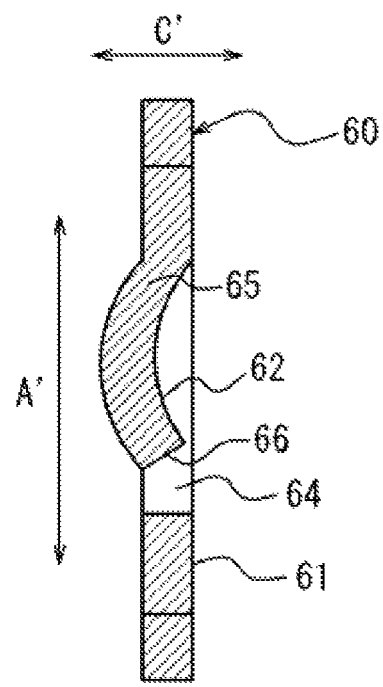

FIGS. 4 to 7 are views schematically illustrating a method of manufacturing the sensor 10 (see FIG. 2 and the like). FIGS. 4 to 6 illustrate a forming step of the needle member 20 (see FIG. 2 and the like) including a forming step of the cutout piece 30 (see FIG. 2 and the like). FIGS. 7(a) through 7(c) illustrate an inserting step of inserting the detection member 40 (see FIG. 2 and the like) into the hollow portion 21. FIG. 4(c) is a cross-sectional view taken along line II-II in FIG. 4(b).

First, the step of forming the needle member 20 will be described. As illustrated in FIG. 4(a), a needle member expanded body 61 and a cutout piece expanded body 62 are punched out from a plate member 60 that is strip-shaped and made of metal, using a press forming machine. The needle member expanded body 61 has a shape in which the needle member 20 after being completed is expanded, and a part of the needle member expanded body 61 is connected to the other portion of the plate member 60 at both ends along a direction A' corresponding to the longitudinal direction A of the needle member 20 after being completed (hereinafter simply described as "longitudinal direction A'). The cutout piece expanded body 62 is partially connected to the needle member expanded body 61 at a proximal end 65 that is one end along the longitudinal direction A. In other words, the cutout piece expanded body 62 has a free end that is an end other than the proximal end 65. A plurality of the cutout piece expanded bodies 62 is formed along a direction B' (hereinafter simply described as the "circumferential direction B'") corresponding to the circumferential direction of the needle member 20 after being completed. A length a of the cutout piece expanded body 62 in the longitudinal direction A' of is less than one half of a length of the needle member 20 in the longitudinal direction A. A length β of the cutout piece expanded body 62 in the circumferential direction B' is less than one fourth of an outer circumferential length of the needle member 20 in the circumferential direction B, and preferably less than one eighth of the outer circumferential length of the needle member 20 in the circumferential direction B. When a total of the lengths β of the cutout piece expanded bodies 62 in the circumferential direction B' is one half or more of the outer circumferential length of the needle member 20 in the circumferential direction B, a strength becomes insufficient. A step of punching out the above-described needle member expanded body 61 will be also described as a needle member expanded body forming step, and a step of punching out the cutout piece expanded body 62 is also described as a cutout piece expanded body forming step.

Next, as illustrated in FIGS. 4(b) and 4(c), the cutout piece expanded body 62 is molded into a shape extruded in a direction perpendicular to a plane in which the plate member 60 extends. At this time, as illustrated in FIG. 4(c), the cutout piece expanded body 62 is curved so that an angle formed with the plane in which the plate member 60 extends becomes large from the proximal end 65 toward a distal end 66 and protrudes most at the distal end 66. A through hole 64 is simultaneously formed along with the protrusion of the cutout piece expanded body 62.

Then, as illustrated in FIG. 5(a), the plate member 60 is arranged between a recessed surface of a first lower mold 91 and a projecting surface of a first upper mold 92 so that a surface from which the cutout piece expanded body 62 protrudes is a lower surface, and the needle member expanded body 61 is curved by press processing. The first lower mold 91 is a mold placed on a lower side with respect to the plate member 60 and is a mold including the recessed surface that presses the lower surface of the needle member expanded body 61. On the recessed surface of the first lower mold 91, a recessed portion such as a groove is formed at a position corresponding to the protruding cutout piece expanded body 62. The first upper mold 92 is a mold that presses an upper surface of the needle member expanded body 61 to form a portion to become the hollow portion 21 of the needle member 20 and is a rod-like mold. The first lower mold 91 includes the recessed portion at the position corresponding to the protruding cutout piece expanded body 62, whereby the needle member expanded body 61 can be pressed into a curved shape while the cutout piece expanded body 62 maintains a state of protruding toward a side of the first lower mold 91.

When a portion (lower half portion illustrated in FIG. 5(a)) of the needle member expanded body 61 is curved by the first lower mold 91 and the first upper mold 92, the plate member 60 is arranged between a recessed surface of a second lower mold 93 and a recessed surface of a second upper mold 94, and the remaining portion (upper half portion illustrated in FIG. 5(b)) of the needle member expanded body 61 is curved by press processing as illustrated in FIG. 5(b). The second lower mold 93 is a mold placed on a lower side with respect to the plate member 60, and is a mold including a recessed surface that forms a portion to be the outer surface of the needle member 20. On the recessed surface of the second lower mold 93, a cylindrical surface or a projecting portion along the outer surface of the needle member 20 is formed at a position corresponding to the protruding cutout piece expanded body 62. The second upper mold 94 is a mold including a recessed surface that forms a portion to be the outer surface of the needle member 20 in the needle member expanded body 61. On the recessed surface of the second upper mold 94, a recessed portion such as a groove is formed at a position corresponding to the protruding cutout piece expanded body 62 similarly to the recessed surface of the first lower mold 91. For this reason, the needle member expanded body 61 is arranged in a substantially cylindrical shape by the second lower mold 93 and the second upper mold 94, and at the same time, the cutout piece expanded body 62 contacting the second lower mold 93 (the lower half illustrated in FIG. 5(*b*)) is pushed by a projecting portion of the second lower mold 93 in a direction opposite to a protruding direction. Meanwhile, the cutout piece expanded body 62 corresponding to the recessed surface of the second upper mold 94 maintains a state of protruding outward from the curved surface.

FIGS. 6(*a*) and 6(*b*) illustrate how the cutout piece expanded body 62 is pushed by the recessed surface of the second lower mold 93. In the protruding cutout piece expanded body 62 as illustrated in FIG. 6(*a*), the distal end 66 that is protruded most is pushed as illustrated in FIG. 6(*b*). Specifically, as illustrated in FIG. 6(*b*), the distal end 66 is pushed so that the cutout piece expanded body 62 rotates around the proximal end 65 while keeping the curved shape. Thus, in a manner similar to that of the cutout piece 30 illustrated in FIG. 2, the cutout piece expanded body 62 is formed in a shape including the first inclined wall portion 33, the second inclined wall portion 34, and the top portion 35.

When the needle member expanded body 61 is formed in a cylindrical shape by the second lower mold 93 and the second upper mold 94, the plate member 60 is arranged between the recessed surface of the second lower mold 93 and the recessed surface of a third upper mold 95 and subjected to press processing, as illustrated in FIG. 5(*c*). The third upper mold 95 is a mold including a recessed surface that forms a portion to become the outer surface of the needle member 20 in the needle member expanded body 61. In a manner similar to that of the recessed surface of the second lower mold 93, the recessed surface of the third upper mold 95 has a cylindrical surface along the outer surface of the needle member 20 at a position corresponding to the protruding cutout piece expanded body 62 or a projecting portion corresponding to the cutout piece expanded body 62 is formed. As a result, at the time of press processing by the second lower mold 93 and the third upper mold, the cutout piece expanded body 62 is pushed in the direction opposite to the protruding direction. That is, as illustrated in FIGS. 6(*a*) and 6(*b*), the cutout piece expanded body 62 is formed as the cutout piece 30 protruding in a direction of the hollow portion 21 in the needle member 20 and including the first inclined wall portion 33, the second inclined wall portion 34, and the top portion 35. A step of forming the cutout piece 30 from the above-described cutout piece expanded body 62 is also described as a cutout piece forming step. Thereafter, the needle member expanded body 61 formed in a cylindrical shape is separated from the other portion of the plate member 60, and the blade surface 26 (see FIG. 2) is formed at an end, whereby the needle member 20 is formed. Thus, by using the press processing, it is possible to incorporate the processing of the cutout piece 30 and the through hole 25 in a step of manufacturing the needle member 20. Therefore, efficient manufacturing is possible. A position of the cutout piece 30 in the needle member 20 can be set with high accuracy.

Next, the inserting step of the detection member 40 will be described. As illustrated to FIG. 7(*a*), the detection member 40 including the detection unit 41, the protective portion 42 having an insulation portion, and the connecting portion 43 having an electroconductive portion are provided. As illustrated in FIG. 7(*b*), the detection member 40 is inserted into the hollow portion 21 from the proximal end side of the needle member 20 through the support member 3 connected to the proximal end of the needle member 20. At this time, since the top portion 35 of the cutout piece 30 is curved inward in the radial direction C, the first inclined wall portion 33 of the cutout piece 30 guides the insertion of the detection member 40 and smooth insertion is possible. Furthermore, the cutout piece 30 curved inward in the radial direction C is provided while being adjacent to the proximal end side of the needle member 20 with respect to the through hole 25, whereby it is suppressed that the detection member 40 protrudes from the through hole 25 and is damaged by contacting the edge of the through hole 25 or the like. By adjusting an insertion length of the detection member 40, it is possible to position the detection unit 41 at a position different from the position of the cutout piece 30 in the longitudinal direction A in a state in which the detection member 40 is inserted, as illustrated in FIG. 7(*c*). For this reason, since the detection unit 41 does not abut on the cutout piece 30 during measurement, it is possible to manufacture a sensor with high accuracy.

Second Embodiment

Figure 8:
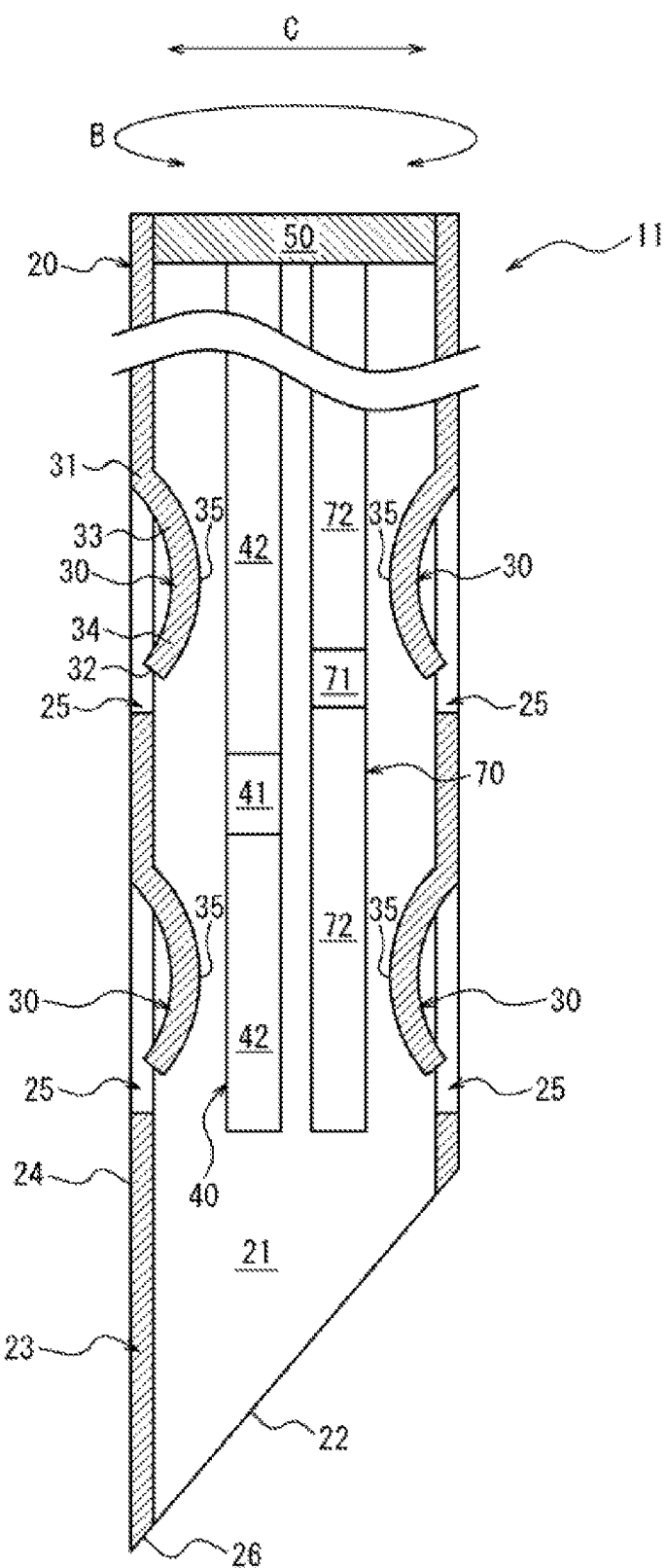
FIG. 8 is a longitudinal sectional view of a sensor according to a second embodiment.

FIG. 8 is a longitudinal sectional view of a sensor 11 according to a second embodiment. The sensor 11 further includes a reference member 70 in addition to the configuration of the sensor 10 of the first embodiment. The reference member 70 includes a reference electrode 71 and an insulation portion 72. The reference electrode 71 is a reference electrode with respect to a working electrode as a detection unit 41. Since the sensor 11 includes the reference electrode 71, there is no need to use a needle member 20 as a reference electrode.

A cutout piece 30 is positioned at a position different from a position of the reference electrode 71 of the reference member 70 in an longitudinal direction A. The reference electrode 71 and the detection unit 41 of a detection member 40 are positioned at mutually different positions in the longitudinal direction A. As a result, even if the detection member 40 and the reference member 70 contact each other, it is possible to suppress a decrease in measurement accuracy due to contact between the detection unit 41 and the reference electrode 71. The detection member 40 and the reference member 70 are fixed by a fixing member 50 on a proximal end side in a state of being separated from each other. When the sensor 11 is manufactured, the detection member 40 and the reference member 70 may be separately inserted into a hollow portion 21, or may be inserted into the hollow portion 21 simultaneously after the detection member 40 and the reference member 70 are fixed at the proximal end side in advance in a state in which the detection member 40 and the reference member 70 are separated from each other. From the viewpoint of suppressing damage to the detection member 40 and the reference member 70, it is preferable that the detection member 40 and the reference member 70 are fixed in advance and then simultaneously insert into the hollow portion 21.

It is also possible to simultaneously perform a plurality of measurements by using a sensor capable of measuring a substance to be measured that is different from a substance measured by the detection unit 41 of the detection member 40 instead of the reference member 70 in FIG. 8. Although FIG. 8 illustrates a case where the detection member 40 and the reference member 70 are used, a member to be inserted into the hollow portion 21 can be arbitrarily set according to a detection method. In a case where a member that detects an optical signal according to an amount or concentration of the substance to be measured is used as the detection member 40, a reference measurement can be performed by using the reference member 70 that measures the influence of disturbance light, interference substances, and the like that influences a measurement.

Third Embodiment

Figure 9:
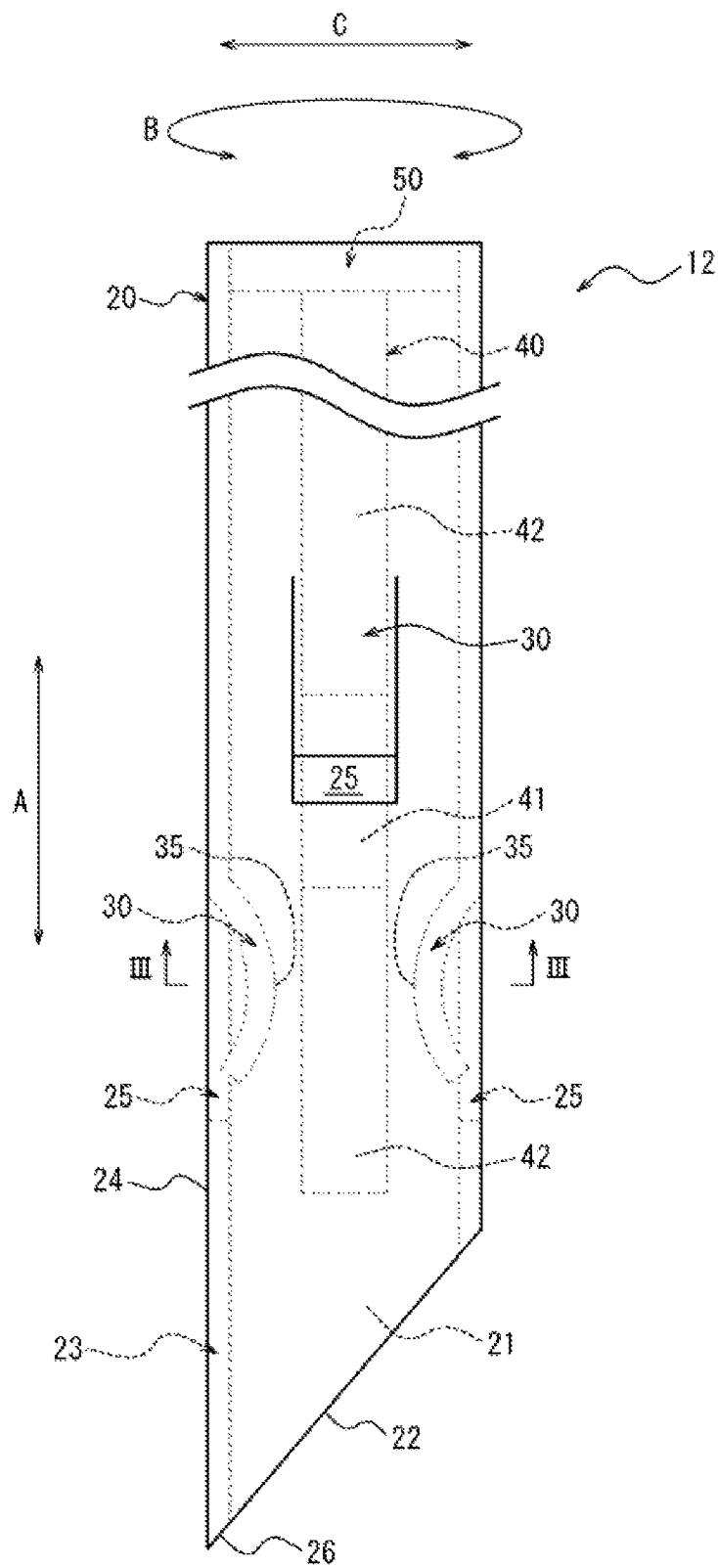
FIG. 9 is a side view of a sensor according to a third embodiment.
Figure 10:
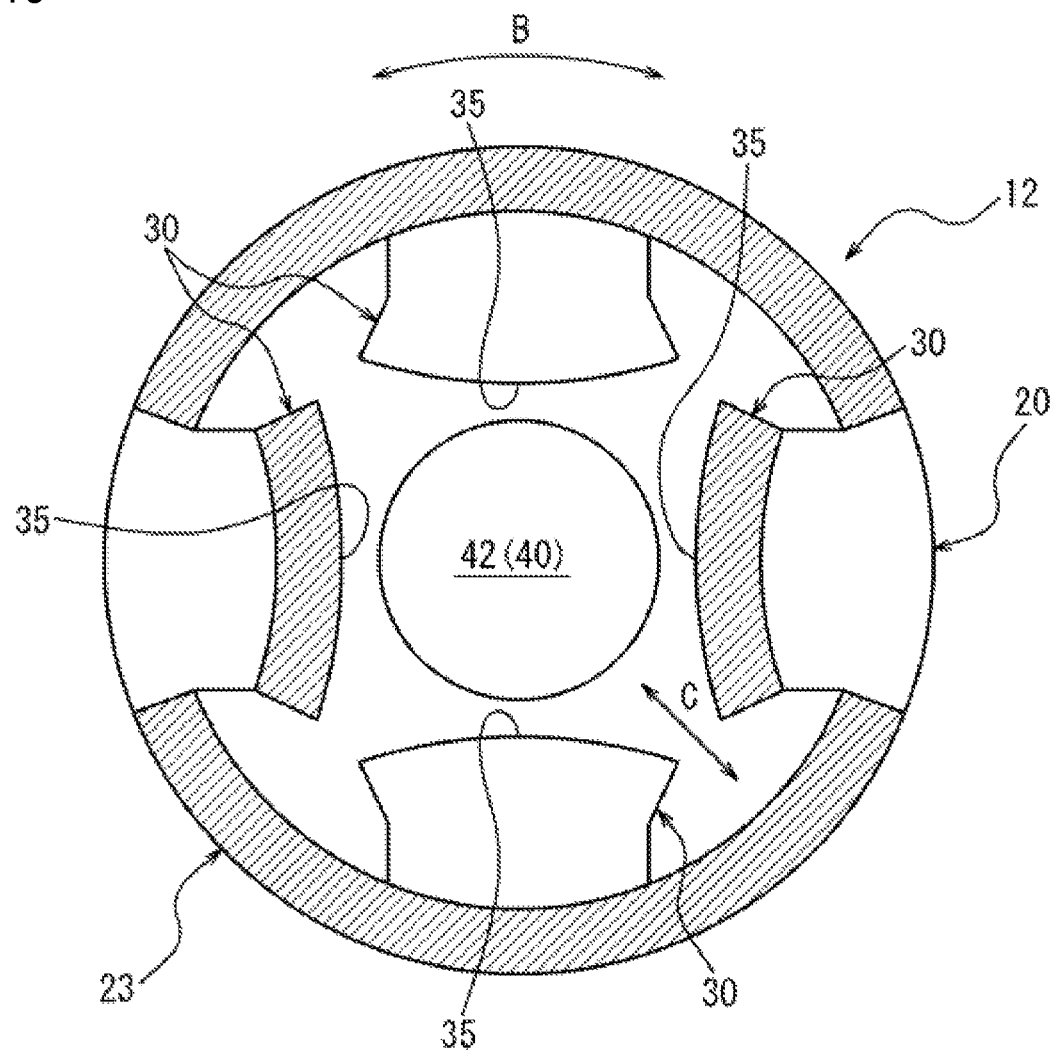
FIG. 10 is a cross-sectional view taken along line III-III in FIG. 9.

FIG. 9 is a side view of a sensor 12 according to a third embodiment. FIG. 10 is a cross-sectional view taken along line III-III of FIG. 9.

As illustrated in FIGS. 9 and 10, the sensor 12 includes a plurality of cutout pieces 30, and the cutout pieces 30 provided at different positions in an longitudinal direction A are arranged at different positions in the circumferential direction B. Specifically, in the sensor 12, a set of two cutout pieces 30 facing each other at certain positions in the longitudinal direction A is formed. In addition, at other positions of the sensor 12 in the longitudinal direction A, another pair of two other cutout pieces 30 is formed at positions rotated about 90° in a circumferential direction B. By arranging the cutout pieces 30 in this manner, the number of cutout pieces 30 formed at the same position in the longitudinal direction A can be suppressed as compared with the sensor 10 of the first embodiment while the outward movement of a detection member 40 in a radial direction C is restricted. Therefore, a strength of the needle member 20 can be improved.

Fourth Embodiment

Figure 11A:
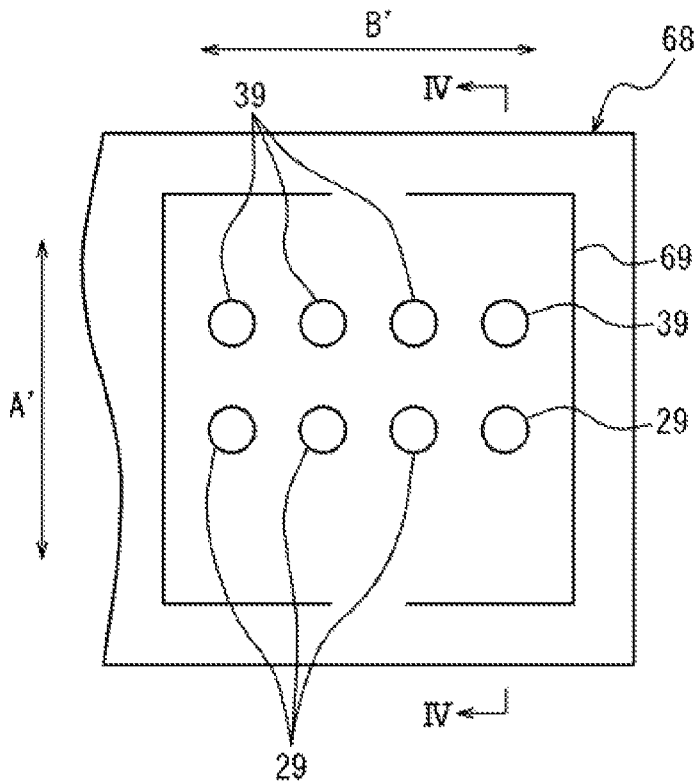
FIGS. 11(a) and 11(b) are views schematically illustrating a part of a step of forming a needle member included in a sensor as a fourth embodiment.
Figure 11B:
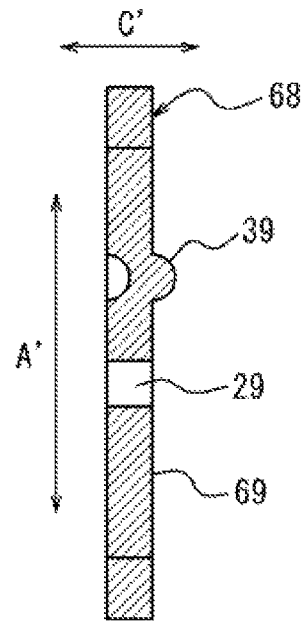

FIGS. 11(a) and 11(b) are views schematically illustrating a part of a step of forming a needle member included in a sensor as a fourth embodiment. FIG. 11(b) is a cross-sectional view taken along line IV-IV of FIG. 11(a). As illustrated in FIGS. 11(a) and 11(b), a needle member expanded body 69 and a through hole 29 are punched out from a plate member 68 that is strip shaped and made of metal, by using a press forming machine. At the same time, by using a press molding machine, a projecting portion 39 as a protruding portion is formed at a position adjacent to the through hole 29 along an longitudinal direction A'. A plurality of through holes 29 and a plurality of projecting portions 39 are provided along a circumferential direction B'. Thus, the sensor of the present embodiment includes the projecting portion 39 instead of the cutout piece 30 of the sensor 10 of the first embodiment, and the movement of a detection member 40 can be restricted by the projecting portion 39. In a sensor of the present embodiment, a radius of the detection member 40 in a predetermined plane orthogonal to an longitudinal direction of the needle member after being completed is preferably larger than a distance between four projecting portions 39 adjacent to each other in a circumferential direction of the needle member (corresponding to a gap between a surface of the projecting portion 39 and a surface of the projecting portion 39). With this configuration, it is possible to reliably restrict that the detection member 40 moves between the projecting portions 39 without abutting on the plurality of projecting portions 39. In the sensor of the present embodiment, as in the sensor 10 of the first embodiment, the projecting portion 39 as the protruding portion is preferably positioned at a position different from a position of a detection unit 41 (see FIG. 2 and the like) in the longitudinal direction of the needle member.

Fifth Embodiment

Figure 12A:
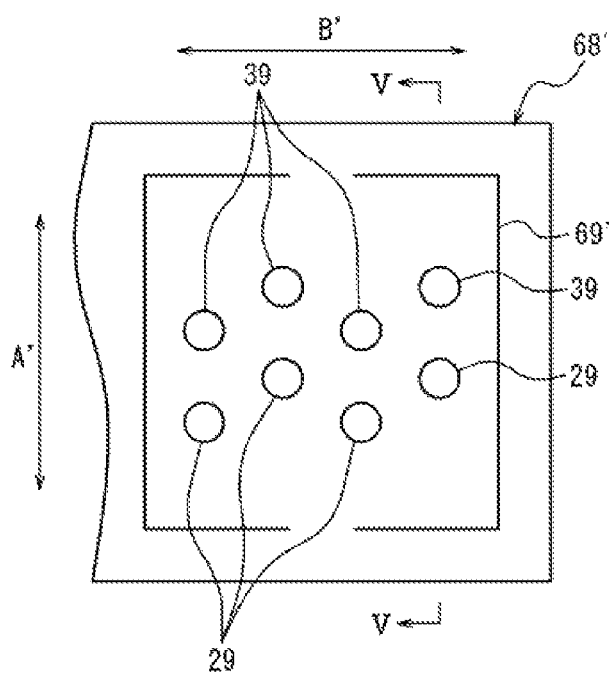
FIGS. 12(a) and 12(b) are views schematically illustrating a part of a step of forming a needle member included in a sensor according to a fifth embodiment.
Figure 12B:
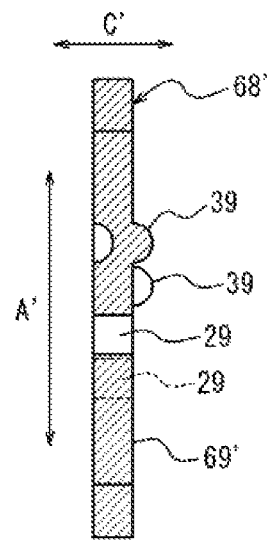

FIGS. 12(a) and 12(b) are views schematically illustrating a part of a step of forming a needle member included in a sensor as a fifth embodiment. FIG. 12(b) is a cross-sectional view taken along line V-V of FIG. 12(a). As illustrated in FIGS. 12(a) and 12(b), unlike the plate member 68 of the fourth embodiment, a plate member 68' of the present embodiment includes a plurality of through holes 29 and projecting portion 39 provided at different positions in an longitudinal direction A' and a circumferential direction B'. By arranging the through holes 29 and the projecting portions 39 in this manner, the numbers of the through holes 29 and the projecting portions 39 formed at the same position in the longitudinal direction A' can be suppressed as compared with the sensor of the fourth embodiment while the movement of a detection member 40 is restricted. Therefore, a strength of the needle member can be improved.

The present disclosure is not limited to the configurations specified in the above-described embodiments, and various modifications can be made without departing from contents described in the claims.

INDUSTRIAL APPLICABILITY

The present disclosure relates to a sensor, a measuring apparatus, and a method of manufacturing the sensor.

REFERENCE SIGNS LIST

1 Measuring apparatus
2 Control unit
3 Support member
4 Housing
10 Sensor
11 Sensor
12 Sensor
20 Needle member
21 Hollow portion
22 Distal end opening
23 Peripheral wall
24 Outer peripheral surface
25 Through hole
26 Blade surface
29 Through hole
30 Cutout piece
31 Proximal end of cutout piece
32 Distal end of cutout piece
33 First inclined wall portion
34 Second inclined wall portion
35 Top portion
39 Projecting portion
40 Detection member
41 Detection unit
42 Protective portion
43 Connecting portion
50 Fixing member
60 Plate member
61 Needle member expanded body
62 Cutout piece expanded body
64 Through hole
65 Proximal end of cutout piece expanded body
66 Distal end of cutout piece expanded body 68, 68' Plate member
69, 69' Needle member expanded body
70 Reference member
71 Reference electrode
72 Insulation portion
91 First lower mold
92 First upper mold
93 Second lower mold
94 Second upper mold
95 Third upper mold
A, A' Longitudinal direction of needle member
B, B' Circumferential direction of needle member
C, C' Radial direction of needle member
R Radius of detection unit
W Minimum distance between cutout pieces adjacent to each other in circumferential direction
θ Angle between first inclined wall portion and peripheral wall at proximal end of sensor in longitudinal sectional view

The invention claimed is:

1. A sensor comprising:
   a needle member defining a hollow portion, wherein the needle member comprises a peripheral wall, and a through hole extends through the peripheral wall;
   an elongated detection member positioned in the hollow portion and extending along a longitudinal direction of the needle member; and
   at least one protruding portion that is adjacent to the through hole along the longitudinal direction, protrudes radially inward from the peripheral wall, and restricts movement of the detection member in a radial direction, wherein the at least one protruding portion comprises:
      a cutout piece that has a first end that is continuous with the peripheral wall, and a second end that is opposite the first end in the longitudinal direction and separated from the peripheral wall,
      wherein the cutout piece includes an inclined wall portion extending inward in the radial direction in a direction from the first end toward the second end.

2. The sensor according to claim 1, wherein the inclined wall portion is a first inclined wall portion, and the cutout piece further includes a second inclined wall portion extending outward in the radial direction of the needle member in a direction from the first inclined wall portion toward the second end.

3. The sensor according to claim 2, wherein the second end of the cutout piece is positioned inward of an outer peripheral surface of the peripheral wall in the radial direction.

4. The sensor according to claim 2, wherein the cutout piece further includes a top portion between the first inclined wall portion and the second inclined wall portion, the top portion being curved so as to project inward in the radial direction.

5. The sensor according to claim 3, wherein the cutout piece further includes a top portion between the first inclined wall portion and the second inclined wall portion, the top portion being curved so as to project inward in the radial direction.

6. The sensor according to claim 1, wherein:
   the at least one protruding portion comprises a plurality of protruding portions, and the plurality of protruding portions are positioned along a predetermined plane orthogonal to the longitudinal direction, and
   on the predetermined plane, a radius of the detection member is larger than a minimum distance between two of the protruding portions that are adjacent to each other in a circumferential direction of the needle member.

7. The sensor according to claim 1, wherein the at least one protruding portion comprises a plurality of protruding portions, the plurality of protruding portions including a first pair of protruding portions located at first longitudinal positions along the needle member, and a second pair of protruding portions located at second longitudinal positions along the needle member that are different from the first longitudinal positions.

8. The sensor according to claim 7, wherein circumferential positions of the first pair of protruding portions around the needle member are different from circumferential positions of the second pair of protruding portions around the needle member.

9. The sensor according to claim 1, wherein:
   the detection member comprises a detection unit, and
   a longitudinal position of the at least one protruding portion along the sensor is different from a longitudinal position of the detection unit along the sensor.

10. A measuring apparatus comprising:
    a sensor comprising:
       a needle member defining a hollow portion, wherein the needle member comprises a peripheral wall, and a through hole extends through the peripheral wall,
       an elongated detection member positioned in the hollow portion and extending along a longitudinal direction of the needle member, and
       at least one protruding portion that is adjacent to the through hole along the longitudinal direction, protrudes radially inward from the peripheral wall, and restricts movement of the detection member in a radial direction, wherein the at least one protruding portion comprises:
          a cutout piece that has a first end that is continuous with the peripheral wall, and a second end that is opposite the first end in the longitudinal direction and separated from the peripheral wall,
          wherein the cutout piece includes an inclined wall portion extending inward in the radial direction in a direction from the first end toward the second end.

11. The measuring apparatus according to claim 10, further comprising:
    a support member from which the sensor extends, wherein a proximal end side of the sensor is attached to the support member.

12. The measuring apparatus according to claim 11, further comprising:
    a control unit configured to analyze a detection result received from the sensor.

13. The measuring apparatus according to claim 12, further comprising:
    a housing that is engaged with the support member and houses the control unit.

14. A method of manufacturing a sensor, the method comprising:
    providing a needle member defining a hollow portion, wherein the needle member comprises a peripheral wall, and a through hole extends through the peripheral wall;
    providing an elongated detection member;
    forming at least one protruding portion adjacent to the through hole along a longitudinal direction of the needle member, wherein the at least one protruding portion protrudes radially inward from the peripheral wall and comprises:
  a cutout piece that has a first end that is continuous with the peripheral wall, and a second end that is opposite the first end in the longitudinal direction and separated from the peripheral wall,
  wherein the cutout piece includes an inclined wall portion extending inward in a radial direction in a direction from the first end toward the second end; and
inserting the detection member into the hollow portion of the needle member from a proximal end side of the needle member such that the detection member extends along the longitudinal direction of the needle member, and the at least one protruding portion restricts movement of the detection member in the radial direction.

\* \* \* \* \*